US006475134B1

(12) United States Patent
Ball et al.

(10) Patent No.: US 6,475,134 B1
(45) Date of Patent: Nov. 5, 2002

(54) DUAL COIL FLOATING MASS TRANSDUCERS

(75) Inventors: Geoffrey R. Ball, Sunnyvale, CA (US); August C. Pombo, San Jose, CA (US); Christopher A. Julian, Los Gatos, CA (US); Eric M. Jaeger, Redwood City, CA (US); Timothy G. Dietz, Fremont, CA (US); Bob H. Katz, Los Gatos, CA (US)

(73) Assignee: Symphonix Devices, Inc., San Jose, CA (US)

( * ) Notice: Subject to any disclaimer, the term of this patent is extended or adjusted under 35 U.S.C. 154(b) by 0 days.

(21) Appl. No.: 09/231,851

(22) Filed: Jan. 14, 1999

Related U.S. Application Data

(63) Continuation of application No. 08/816,115, filed on Mar. 11, 1997, which is a continuation-in-part of application No. 08/582,301, filed on Jan. 3, 1996, now Pat. No. 5,800,336, which is a continuation-in-part of application No. 08/568,006, filed on Dec. 6, 1995, which is a continuation-in-part of application No. 08/368,219, filed on Jan. 3, 1995, now Pat. No. 5,624,376, which is a continuation-in-part of application No. 08/225,153, filed on Apr. 8, 1994, now Pat. No. 5,554,096, which is a continuation-in-part of application No. 08/087,618, filed on Jul. 1, 1993, now Pat. No. 5,456,654.

(51) Int. Cl.[7] .................................................. A61F 17/43
(52) U.S. Cl. ............................................ 600/25; 29/605
(58) Field of Search ............................... 600/25; 29/605

(56) References Cited

U.S. PATENT DOCUMENTS

| | | | |
|---|---|---|---|
| 3,594,514 | A | 7/1971 | Wingrove |
| 3,712,962 | A | 1/1973 | Epley |
| 3,752,939 | A | 8/1973 | Bartz |
| 3,764,748 | A | 10/1973 | Branch et al. |
| 3,870,832 | A | 3/1975 | Fredrickson |
| 3,882,285 | A | 5/1975 | Nunley et al. |
| 4,063,048 | A | 12/1977 | Kissiah, Jr. |
| 4,063,049 | A | 12/1977 | Pipitone et al. |
| 4,352,960 | A | 10/1982 | Dormer et al. |
| 4,357,497 | A | 11/1982 | Hochmair et al. |
| 4,606,329 | A | 8/1986 | Hough |
| 4,611,598 | A | 9/1986 | Hortman et al. |
| 4,612,915 | A | 9/1986 | Hough et al. |
| 4,628,907 | A | 12/1986 | Epley |
| 4,696,287 | A | 9/1987 | Hortmann et al. |
| 4,728,327 | A | 3/1988 | Gersdorff |
| 4,729,366 | A | 3/1988 | Schaffer |
| 4,756,312 | A | 7/1988 | Epley |
| 4,776,322 | A | 10/1988 | Hough et al. |
| 4,800,884 | A | 1/1989 | Heide et al. |
| 4,817,607 | A | 4/1989 | Tatge |
| 4,817,609 | A | 4/1989 | Perkins et al. |
| 4,832,051 | A | 5/1989 | Jarvik et al. |
| 4,840,178 | A | 6/1989 | Heide et al. |

(List continued on next page.)

FOREIGN PATENT DOCUMENTS

| | | |
|---|---|---|
| GB | 1440724 | 4/1997 |

OTHER PUBLICATIONS

Baumfield, A. et al., "Performance of Assistive Listening Devices Using Insertion Gain Measures," *Scand Audiol*, 22:43–46 (1993).

(List continued on next page.)

*Primary Examiner*—John P. Lacyk
(74) *Attorney, Agent, or Firm*—Townsend and Townsend and Crew LLP

(57) ABSTRACT

A dual coil floating mass transducer for assisting a person's hearing is provided. Inertial vibration of the housing of the floating mass transducer produces vibrations in the inner ear. A magnet is disposed within the housing biased by silicone springs so that friction is reduced between the magnet and the interior surface of the housing. Two coils reside within grooves in the exterior of the housing which cause the magnet to vibrate when an electrical signal is applied to the coils.

16 Claims, 11 Drawing Sheets

U.S. PATENT DOCUMENTS

| | | | |
|---|---|---|---|
| 4,918,745 | A | 4/1990 | Hutchison |
| 4,936,305 | A | 6/1990 | Ashtiani et al. |
| 4,957,478 | A | 9/1990 | Maniglia |
| 4,969,900 | A | 11/1990 | Fleischer |
| 4,988,333 | A | 1/1991 | Engebretson et al. |
| 5,015,224 | A | 5/1991 | Maniglia |
| 5,015,225 | A | 5/1991 | Hough et al. |
| 5,047,994 | A | 9/1991 | Lenhardt et al. |
| 5,085,628 | A | 2/1992 | Engebretson et al. |
| 5,163,957 | A | 11/1992 | Sade et al. |
| 5,220,918 | A | 6/1993 | Heide et al. |
| 5,257,623 | A | 11/1993 | Karasev et al. |
| 5,259,032 | A | 11/1993 | Perkins et al. |
| 5,259,033 | A | 11/1993 | Goodings et al. |
| 5,277,694 | A | 1/1994 | Leysieffer et al. |
| 5,282,858 | A | 2/1994 | Bisch et al. |
| 5,295,193 | A | 3/1994 | Ono |
| 5,338,287 | A | 8/1994 | Miller et al. |
| 5,356,430 | A | 10/1994 | Nadol, Jr. |
| 5,447,489 | A | 9/1995 | Issalene et al. |
| 5,456,654 | A | 10/1995 | Ball |
| 5,531,787 | A | 7/1996 | Lesinski et al. |
| 5,554,096 | A | 9/1996 | Ball |
| 5,624,376 | A | 4/1997 | Ball et al. |

OTHER PUBLICATIONS

Buchman E., et al., "On the Transmission of Sound Generated by an Electromagnetic Device from the Mastoid Process to the Petrou . . . ," *J. Acoust Soc. Am*, 90:895–903 (1991).

Goode, R.L., "Implantable Hearing Devices," *Medical Clinics of North America*, 75:1261–66 (1991).

Goode, R.L., "Current Sattus of Electromagnetic Implantable Hearing Aids," *Otolarygologic Clinics of North America*, 22:201–09.

McGee, T.M. et al., "Electromagnetic Semi–Implantable Hearing Device: Phase I. Clinical Trials," *Laryngoscope*, 101:355 (1991).

Häkansson, B. et al., "Percutaneous v. Transcutaneous Transducers for Hearing by Direct Bone Conduction" *Otolaryngol Head Ne* . . . , 102:339 (1990).

Heide, J. et al., "Development of Semi–Implantable Hearing Device," *Adv. Audiol.*, 4:32–43 (1988).

Hough, J. et al., "A Middle Ear Implantable Hearing Device for Controlled Amplification of Sound in the Human: A Preliminary Report," *Laryngoscope*, 97:141–51 (1987).

Kartush, J.M. et al., "Electromagnetic Semi–Implantable Hearing Device: An Update," *Otolaryngol Head Neck Surg.*, 104:150 (1991).

Lenkamakas, E., "Otally Implantable Hearing Aid Device," *Transplants and Implants in Othology II*, pp. 371–375 (1992).

Maniglia, A.J. et al. "Design, Development and Analysis of a Newer Electro–Magnetic Semi–Implantable Middle Ear Hearing Device," *Transplants* and Implants in Otology II, pp. 365–369 (1992).

Parisier, S.C. et al., "Cochlear Implants: Indications and Technology," *Medical Clinics of North America*, 75:1267–76 (1991).

Suzuki, J. et al., "Further Clinical Experiences with Middle–Ear Implantable Hearing Aids: Indications and Sound Quality Evaluation," *ORL J Otorhinolaryngol Relat Spec.*, 51:229–234 (1989).

Weber, B.A et al., "Application of an Imploantable Bone Conduction Hearing Device to Patients with Unilateral Sensorineural Hearing," *Laryngoscope*, 102:538–42 (1992).

Yanagihara, N. et al., "Development of an Implantable Hearing Aid Using a Piezoelectric Vibrator of Bimorph Design: State of the Art," *Otolaryngol Head Neck Surg.*, 92:706 (1984).

DUAL COIL FLOATING MASS TRANSDUCERS

This application is a continuation of Ser. No. 08/816,115 filed Mar. 11, 1997, which is a Continuation-In-Part of application Ser. No. 08/582,301, filed Jan. 3, 1996, and issued as U.S. Pat. No. 5,800,336 which is a Continuation-In-Part of application Ser. No. 08/568,006 filed Dec. 6, 1995, which is a Continuation-In-Part of application Ser. No. 08/368,219 filed Jan. 3, 1995, and issued as U.S. Pat. No. 5,624,376 which is a Continuation-In-Part of application No. Ser. 08/225,153 filed on Apr. 8, 1994, and issued as U.S. Pat. No. 5,554,096 which is a Continuation-In-Part application of application No. Ser. 08/087,618 filed on Jul. 1, 1993, and issued as U.S. Pat. No. 5,456,654. The full disclosures of each of these applications is hereby incorporated by reference for all purposes.

BACKGROUND OF THE INVENTION

The present invention relates to the field of assisting hearing in persons and particularly to the field of transducers for producing vibrations in the inner ear.

The seemingly simple act of hearing is a task that can easily be taken for granted. The hearing mechanism is a complex system of levers, membranes, fluid reservoirs, neurons and hair cells which must all work together an order to deliver nervous stimuli to the brain where this information is compiled into the higher level perception we think of as sound.

As the human hearing system encompasses a complicated mix of acoustic, mechanical and neurological systems, there is ample opportunity for something to go wrong. Unfortunately this is often the case. It is estimated that one out of every ten people suffer some form of hearing loss. Surprisingly, many patients who suffer from hearing loss take no action in the form of treatment for the condition. In many ways, hearing is becoming more important as the pace of life and decision making increases as we move toward an information Unfortunately this is often the case. It is estimated that one out of every ten people suffer some form of hearing loss. Surprisingly, many patients who suffer from hearing loss take no action in the form of treatment for the condition. In many ways, hearing is becoming more important as the pace of life and decision making increases as we move toward an information based society. Unfortunately for the hearing impaired, success in many professional and social situations may be becoming more dependent on effective hearing.

Various types of hearing aids have been developed to restore or improve hearing for the hearing impaired. With conventional hearing aids, sound is detected by a microphone, amplified using amplification circuitry, and transmitted in the form of acoustical energy by a speaker or another type of transducer into the middle ear by way of the tympanic membrane. Often the acoustical energy delivered by the speaker is detected by the microphone, causing a high-pitched feedback whistle. Moreover, the amplified sound produced by conventional hearing aids normally includes a significant amount of distortion.

Attempts have been made to eliminate the feedback and distortion problems associated with conventional hearing aid systems. These attempts have yielded devices which convert sound waves into electromagnetic fields having the same frequencies as the sound waves. A microphone detects the sound waves, which are both amplified and converted to an electrical current. A coil winding is held stationary by being attached to a nonvibrating structure within the middle ear. The current is delivered to the coil to generate an electromagnetic field. A separate magnet is attached to an ossicle within the middle ear so that the magnetic field of the magnet interacts with the magnetic field of the coil. The magnet vibrates in response to the interaction of the magnetic fields, causing vibration of the bones of the middle ear.

Existing electromagnetic transducers present several problems. Many are installed using complex surgical procedures which present the usual risks associated with major surgery and which also require disarticulating (disconnecting) one or more of the bones of the middle ear. Disarticulation deprives the patient of any residual hearing he or she may have had prior to surgery, placing the patient in a worsened position if the implanted device is later found to be ineffective in improving the patient's hearing.

Although the Floating Mass Transducer (FMT) developed by the present assignee is a pioneering technology that has succeeded where prior art devices have failed, improved floating mass transducers would be desirable to provide hearing assistance.

SUMMARY OF THE INVENTION

The present invention provides an improved dual coil floating mass transducer for assisting a person's hearing. Inertial vibration of the housing of the floating mass transducer produces vibrations in the inner ear. A magnet is disposed within the housing biased by biasing mechanisms so that friction is reduced between the magnet and the interior surface of the housing. Two coils reside within grooves in the exterior of the housing which cause the magnet to vibrate when an electrical signal is applied to the coils.

With one aspect of the invention, an apparatus for improving hearing comprises: a housing; at least one coil coupled to an exterior of the housing; and a magnet positioned within the housing so that an electrical signal through the at least one coil causes the magnet to vibrate relative to the housing, wherein vibration of the magnet causes inertial vibration of the housing in order to improve hearing. Typically, a pair of oppositely wound coils are utilized.

With another aspect of the invention, a system for improving hearing comprises: an audio processor that generates electrical signals in response to ambient sounds; and a transducer electrically coupled to the audio processor comprising a housing; at least one coil coupled to an exterior of the housing; and a magnet positioned within the housing so that an electrical signal through the at least one coil causes the magnet to vibrate relative to the housing, wherein vibration of the magnet causes inertial vibration of the housing in order to improve hearing.

With another aspect of the invention, a method of manufacturing a hearing device comprises the steps of: providing a cylindrical housing; placing a magnet within the housing; biasing the magnet within the housing; sealing the housing; and wrapping at least one coil around an exterior of the housing.

Additional aspects and embodiments of the present invention will become apparent upon a perusal of the following detailed description and accompanying drawings.

DETAILED DESCRIPTION OF THE PREFERRED EMBODIMENTS

The present invention provides innovative floating mass transducers for assisting hearing. The following description describes preferred embodiments of the invention; however, the description is for purposes of illustration and not limitation. For example, although specific steps are described for making a floating mass transducer, the order that the steps are described should not be taken as an implication that the steps must be performed in any particular order.

Figure 1:
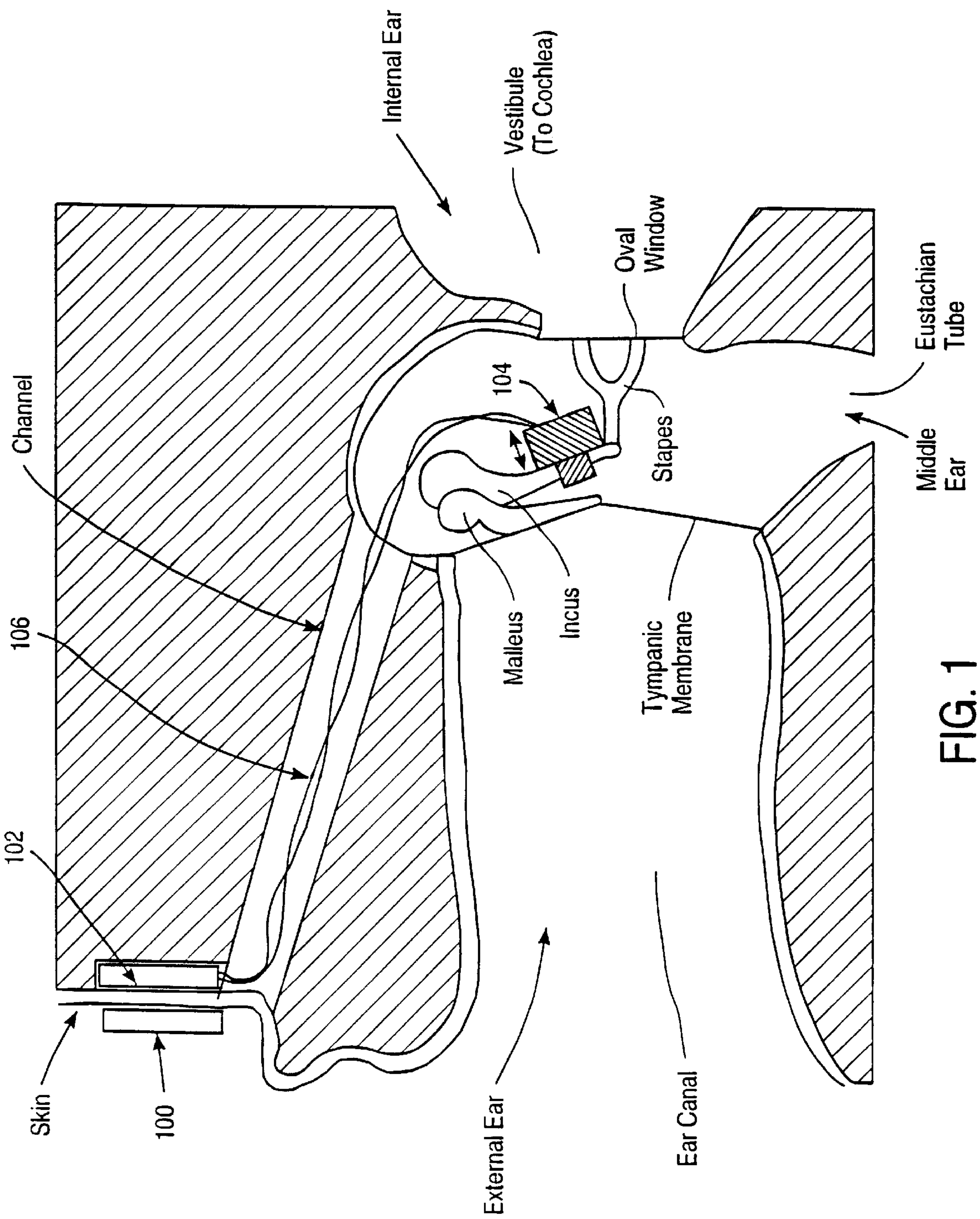
FIG. 1 is a schematic representation of a portion of the auditory system showing a floating mass transducer positioned for receiving electrical signals from a subcutaneous coil inductively coupled to an external audio processor positioned outside a patient's head.

FIG. 1 is a schematic representation of a portion of the auditory system showing a floating mass transducer positioned for receiving electrical signals from a subcutaneous coil inductively coupled to an external audio processor positioned outside a patient's head. An audio processor 100 receives ambient sounds and typically processes the sounds to suit the needs of the user before transmitting signals to an implanted receiver 102. The audio processor typically includes a microphone, circuitry performing both signal processing and signal modulation, a battery, and a coil to transmit signals via varying magnetic fields to the receiver. An audio processor that may be utilized with the present invention is described in U.S. application Ser. No. 08/526,129, filed Sep. 7, 1995, which is hereby incorporated by reference for all purposes. Additionally, an implanted audio processor may be utilized with the invention.

Receiver 102 includes a coil that transcutaneously receives signals from she audio processor in the form of varying magnetic fields in order to generate electrical signals. The receiver typically includes a demodulator to demodulate the electrical signals which are then transmitted to a floating mass transducer 104 via leads 106. The leads reach the middle ear through a surgically created channel in the temporal bone.

The electrical signals cause a floating mass within the housing of the floating mass transducer to vibrate. As will be described in more detail in reference to the remaining figures, the floating mass may be a magnet which vibrates in response to coils connected to the housing that receive the electrical signals and generate varying magnetic fields. The magnetic fields interact with the magnetic fields of the magnet which causes the magnet to vibrate. The inertial vibration of the magnet causes the housing of the floating mass transducer to vibrate relative to the magnet. As shown, the housing is connected to an ossicle, the incus, by a clip so the vibration of the housing (see, e.g., double-headed arrow in FIG. 1) will vibrate the incus resulting in perception of sound by the user.

The above description of the operation of a floating mass transducer with reference to FIG. 1 illustrates one embodiment of the floating mass transducer. Other techniques for implantation, attachment and utilization of floating mass transducers are described in the U.S. Patents and Applications previously incorporated by reference. The following will now focus on improved floating mass transducer design.

Figure 2:
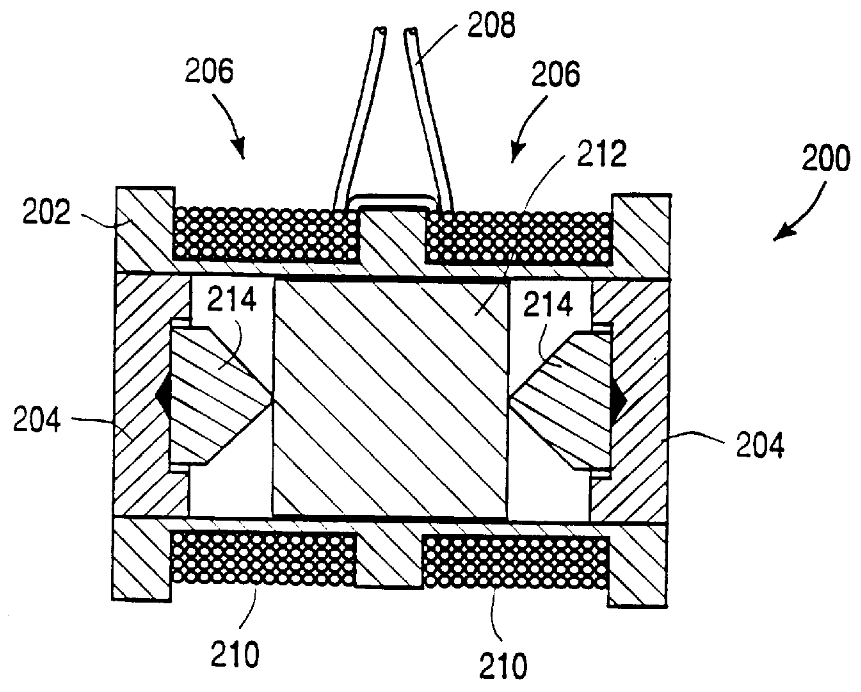
FIG. 2 is a cross-sectional view of an embodiment of a floating mass transducer.

FIG. 2 is a cross-sectional view of an embodiment of a floating mass transducer. A floating mass transducer 200 includes a cylindrical housing 202 which is sealed by two end plates 204. In preferred embodiments, the housing is composed of titanium and the end plates are laser welded to hermetically seal the housing.

The cylindrical housing includes a pair of grooves 206. The grooves are designed to retain wrapped wire that form coils much like bobbins retain thread. A wire 208 is wound around one groove, crosses over to the other groove and is wound around the other groove. Accordingly, coils 210 are formed in each groove. In preferred embodiments, the coils are wound around the housing in opposite directions. Additionally, each coil may include six "layers" of wire, which is preferably insulated gold wire.

Within the housing is a cylindrical magnet 212. The diameter of the magnet is less than the inner diameter of the housing which allows the magnet to move or "float" within the housing. The magnet is biased within the housing by a pair of silicone springs 212 so that the poles of the magnet are generally surrounded by coils 210. The silicone springs act like springs which allow the magnet to vibrate relative to the housing resulting in inertial vibration of the housing. As shown, each silicone spring is retained within an indentation in an end plate. The silicone springs may be glued or otherwise secured within the indentations.

Although the floating mass transducer shown in FIG. 2 has excellent audio characteristics, the silicone springs rely on surface friction to retain the magnet centered within the housing so that there is minimal friction with the interior surface of the housing. It has been discovered that it would be preferable to have the silicone springs positively retain the magnet centered within the housing not in contact with the interior surface of the housing. One way to achieve this is to create indentation in the ends of the magnet such that the ends of the silicone springs nearest the magnet will reside in the indentations in the magnet. It may preferable, however, to accomplish the same result without creating indentations in the magnet.

Figure 3:
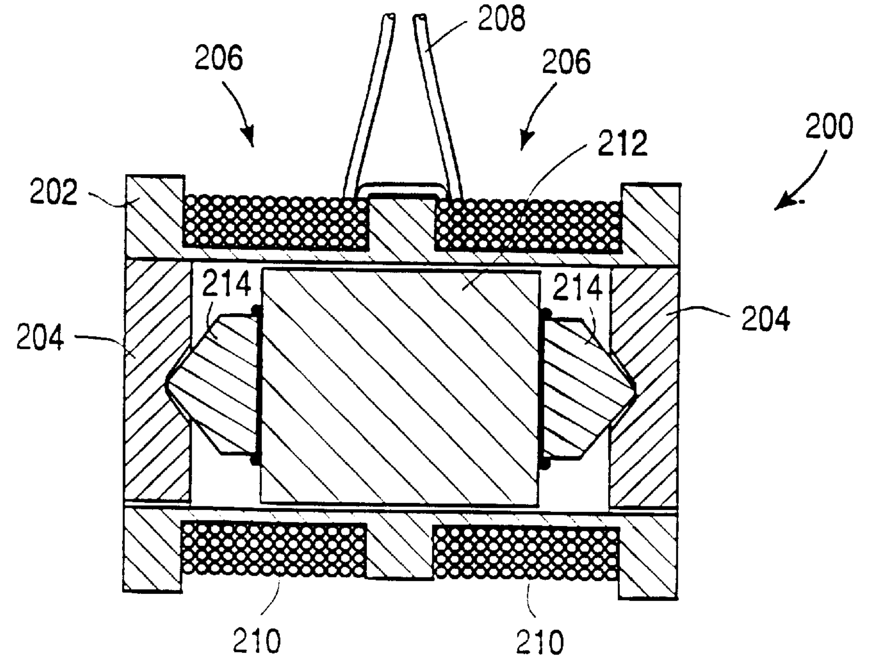
FIG. 3 is a cross-sectional view of another embodiment of a floating mass transducer.

FIG. 3 is a cross-sectional view of another embodiment of a floating mass transducer. For simplicity, the reference numerals utilized in FIG. 3 refer to corresponding structures an FIG. 2. However, as is apparent when the figures are compared, the silicone springs have been reversed as follows.

Silicone springs 214 are secured to magnet 212 by, e.g., an adhesive. End plates 204 have indentations within which an end of the silicone springs are retained. In this manner, the magnet biased within the center of the housing but not in contact with the interior surface of the housing. FIGS. 4A–4M will illustrate a process of making the floating mass transducer shown in FIG. 3.

Figure 4A:
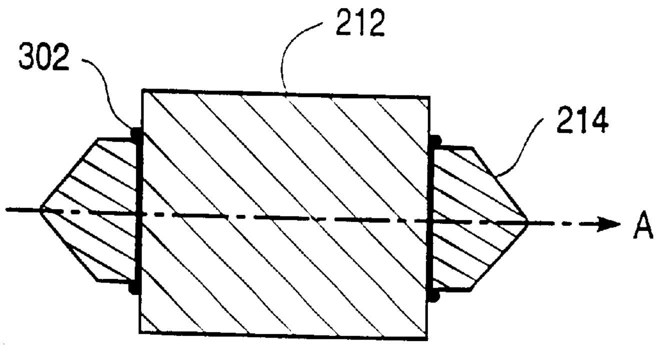
FIG. 4A shows views of a magnet and biasing mechanisms.

FIG. 4A shows views of a magnet and biasing mechanisms. The Left side of the figure shows a cross-sectional view including magnet 212 and silicone springs 214. The silicone springs are secured to the magnet by an adhesive 302. The right side of the figure shows the magnet and biasing mechanisms along the line indicated by A.

Figure 4B:
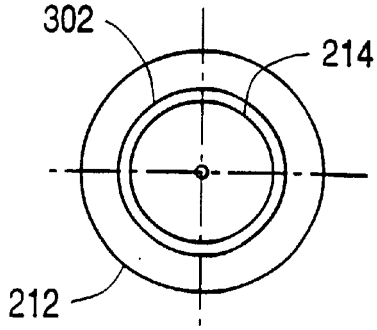
FIG. 4B shows a cross-sectional view of a cylindrical housing with one end open.

FIG. 4B shows a cross-sectional view of a cylindrical housing with one end open. Cylindrical housing 202 is shown with one end plate 204 secured to seal up one end of the housing. in a preferred embodiment, the end plates are laser welded.

Figure 4C:
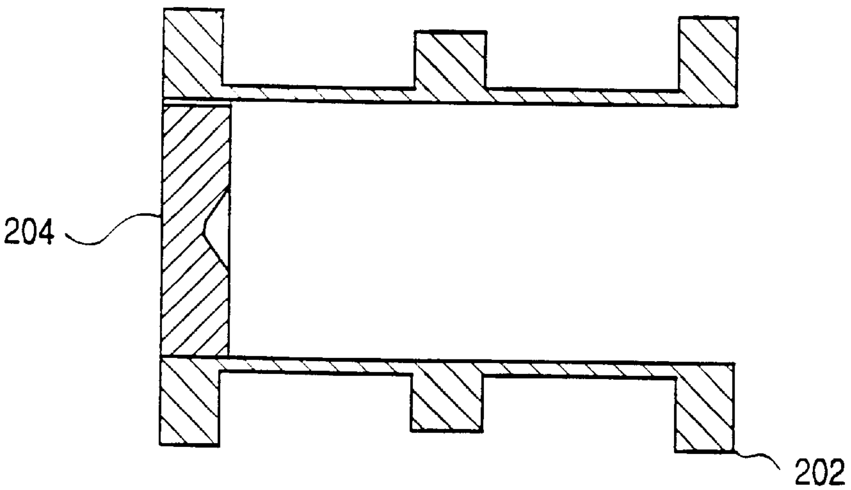
FIG. 4C shows a cross-sectional view of a magnet and biasing mechanisms within the cylindrical housing.
Figure 4D:
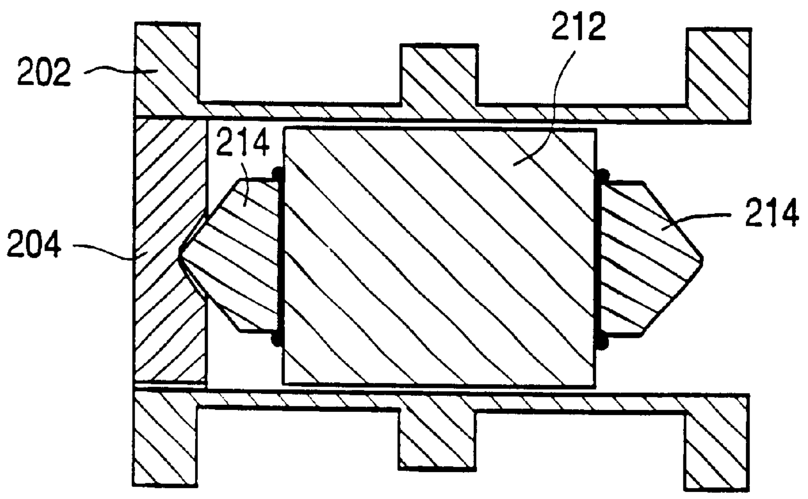
FIG. 4D shows a cross-sectional view of a magnet biased within the sealed cylindrical housing.

FIG. 4C shows a cross-sectional view of a magnet and biasing mechanisms within the cylindrical housing. The magnet and biasing mechanisms are placed within the cylindrical housing through the open end. FIG. 4D shows a cross-sectional view of a magnet biased within the sealed cylindrical housing. End plate 204 is secured to the open end of the housing and is preferably laser welded to seal the housing.

Figure 4E:
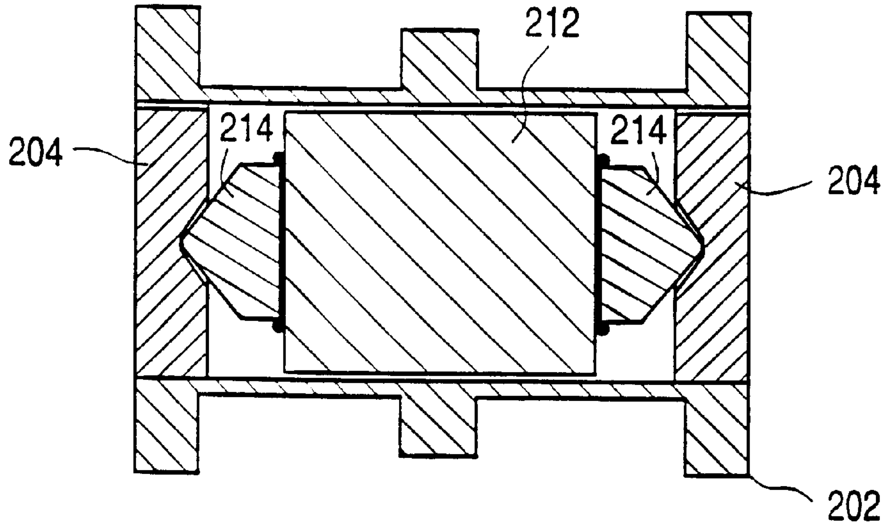
FIG. 4E illustrates beginning the process of wrapping a wire around a groove in the cylindrical housing.

FIG. 4E illustrates beginning the process of wrapping a wire around a groove in the cylindrical housing. Preferably, the wire includes a low resistance, biocompatible material. The housing is placed in a lathe 322 (although not a traditional lathe, the apparatus will be called that since both rotate objects). Initially, wire 208 is wrapped around the housing within one of grooves 206 starting at a flange 353 between the two grooves. A medical grade adhesive like Loctite glue may be placed within the groove to help hold the wire in place within the groove. As indicated, the lathe is turned in a counter-clockwise direction. Although the actual direction of rotation is not critical, it is being specified here to more clearly demonstrate the process of making the floating mass transducer.

Figure 4F:
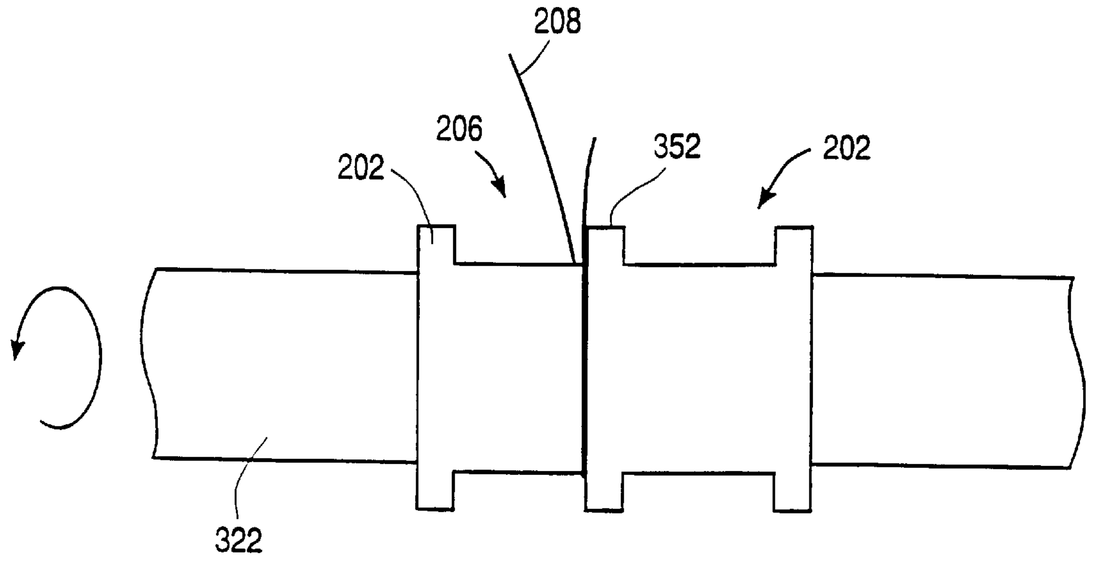
FIG. 4F illustrates the process of wrapping the wire around the groove in the cylindrical housing.

FIG. 4F illustrates the process of wrapping the wire around the groove in the cylindrical housing. As lathe 322 rotates the housing, wire 208 is wrapped around the housing in the groove in the direction of the arrow (the windings have been spaced out to more clearly illustrate this point). Once the wire reaches an end of the groove, the wire continues to be wound in the groove but toward the other end of the groove. As mentioned earlier, this is similar to how thread is wound onto a bobbin or spool. In a preferred embodiment, the wire is wound six layers deep which would place the wire at the center of the housing.

Figure 4G:
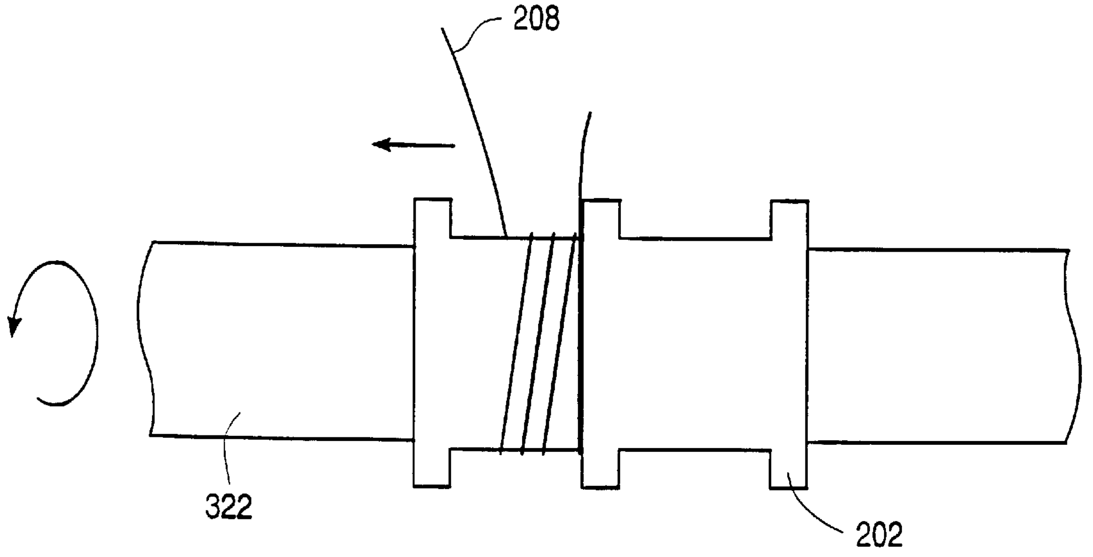
FIG. 4G shows a cross-sectional view of crossing the wire over to another groove in the cylindrical housing.

FIG. 4G shows a cross-sectional view of crossing the wire over to another groove in the cylindrical housing. When one coil has been wound within a groove, the lathe is stopped and the wire is crossed over flange 352 between the grooves before the wire is wound within the other groove.

Figure 4H:
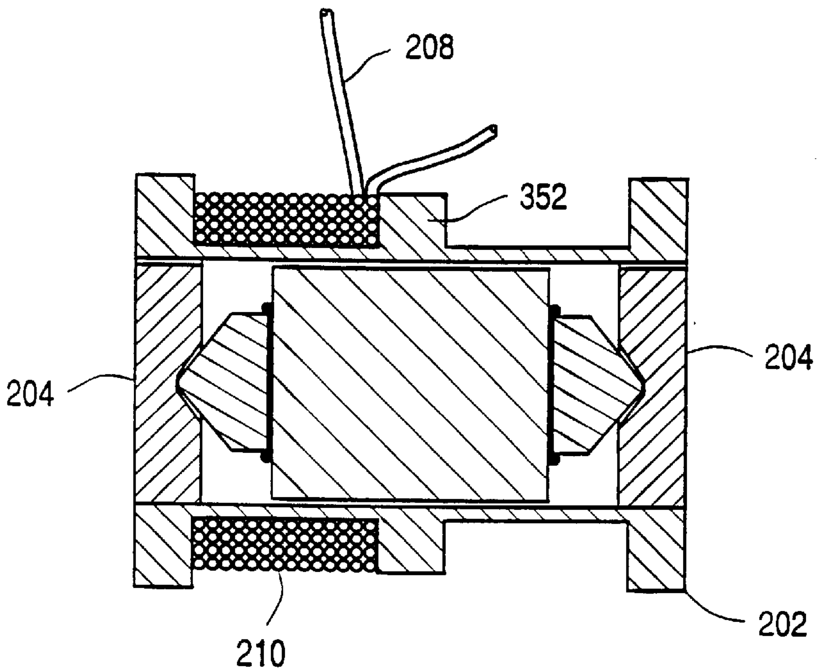
FIG. 4H illustrates the process of wrapping the wire around the other groove in the cylindrical housing.
Figure 4I:
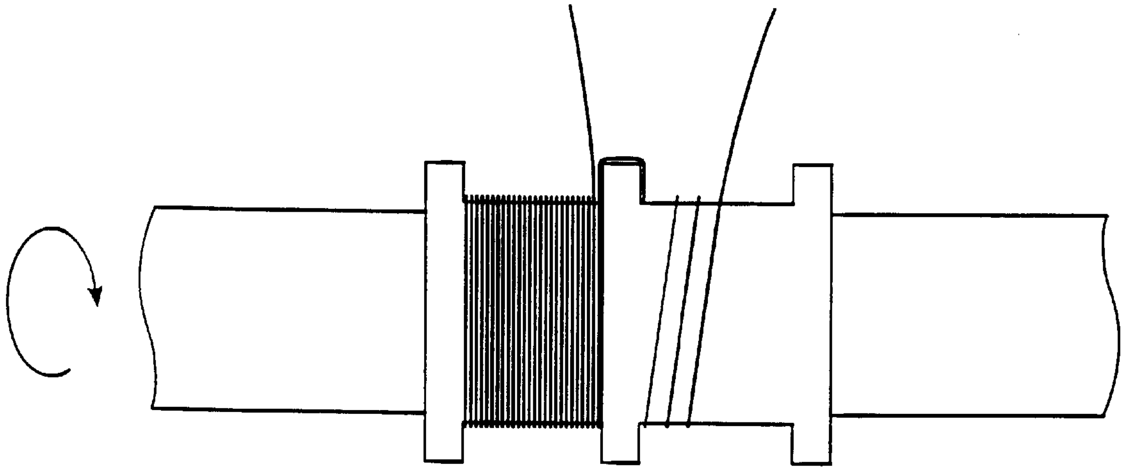
FIG. 4I shows a cross-sectional view of thicker leads connected to the ends of the wire wrapped around the cylindrical housing that form a pair of coils of the floating mass transducer.

FIG. 4H illustrates the process of wrapping the wire around the other groove in the cylindrical housing. The wire is wound around the other groove in a manner similar to the manner that was described in reference to FIGS. 4E and 4F except that the lathe now rotates the housing in the opposite direction, or clock-wise as indicated. Again the windings are shown spaced out for clarity.

Once the wire has been wound around the housing within the second groove to create a coil the same size as the first coil, both ends of the wire are near the center of the housing. Thicker leads 372 may then welded to the thinner wire as shown in the cross-section view of FIG. 4I.

Figure 4J:
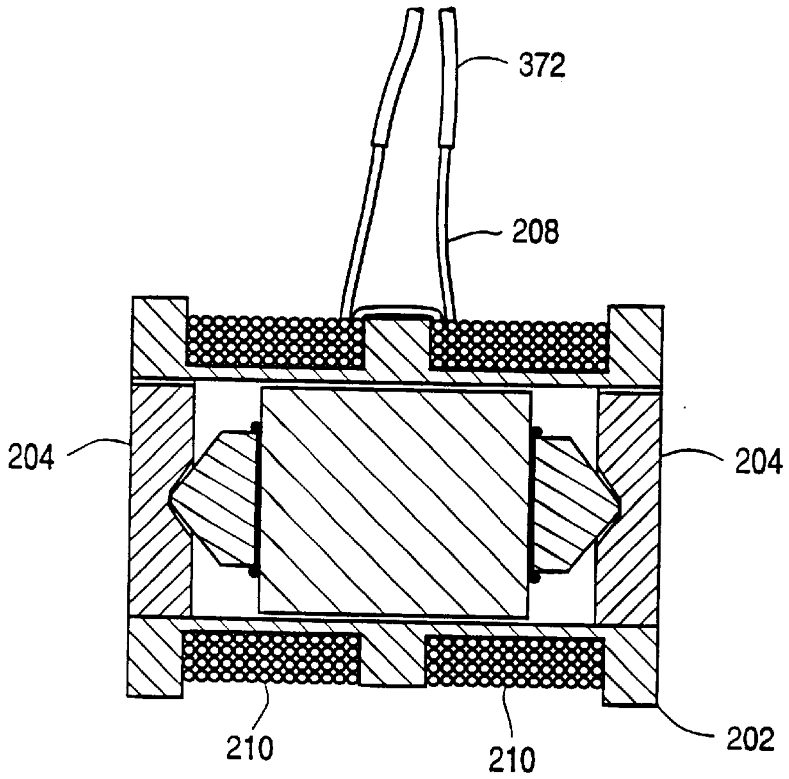
FIG. 4J shows a cross-section view of the thicker leads wrapped around the cylindrical housing.

FIG. 4J shows a cross-section view of the thicker leads wrapped around the cylindrical housing. The thicker leads are shown wrapped around the housing one time which may alleviate stress on the weld between the leads and the wire.

Figure 4K:
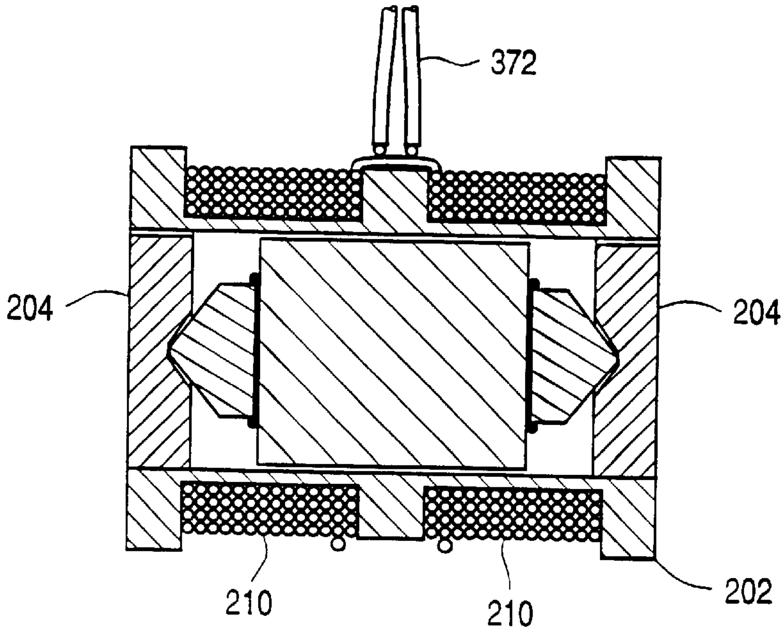
FIG. 4K shows a clip for connecting the floating mass transducer to an ossicle within the inner ear.

FIG. 4K shows a clip for connecting the floating mass transducer to an ossicle within the inner ear. A clip 402 has an end 404 for attachment to the housing of the floating mass transducer and an end 406 that is curved in the form of a “C” so that it may be easily clamped on an ossicle like the incus. At end 406, the clip has two pairs of opposing prongs that, when bent, allow for attachment to an ossicle. Although two pairs of prongs are shown, more may be utilized.

Figure 4L:
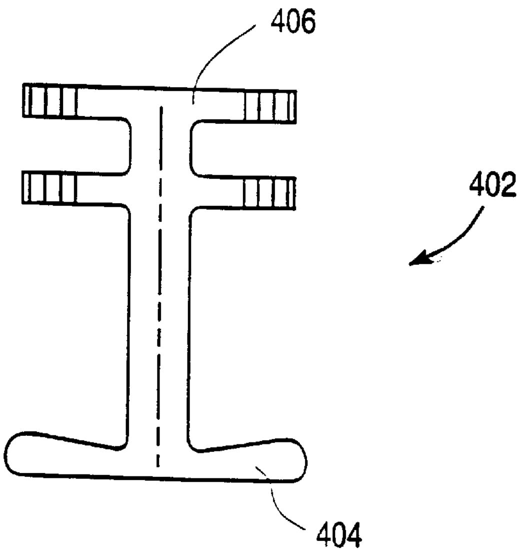
FIG. 4L shows the clip secured to the floating mass transducer.

FIG. 4L shows the clip secured to the floating mass transducer. End 404 is wrapped and welded around one end of housing 202 of the floating mass transducer as shown. End 406 of the clip is then available for being clamped on an ossicle. As shown, the clip may be clamped onto the incus near where the incus contacts the stapes.

Figure 4M:
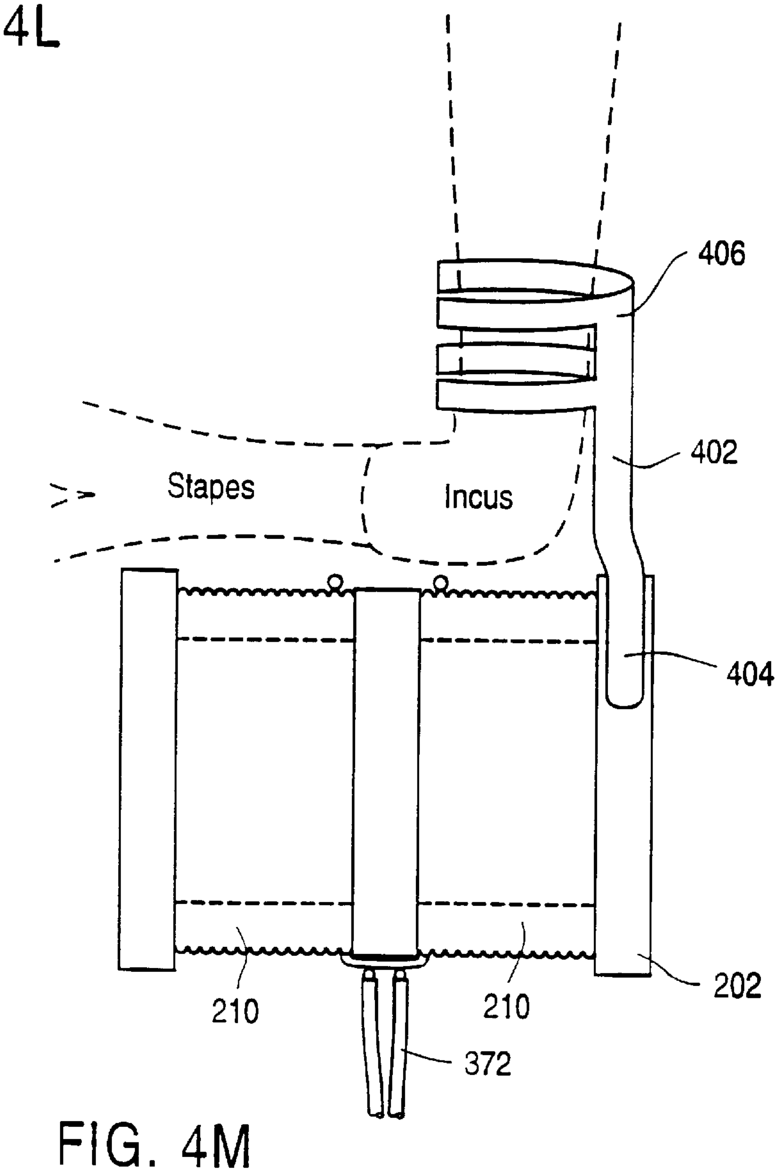
FIG. 4M shows views of a floating mass transducer that as ready to be implanted in a patient.
Figure 4N:
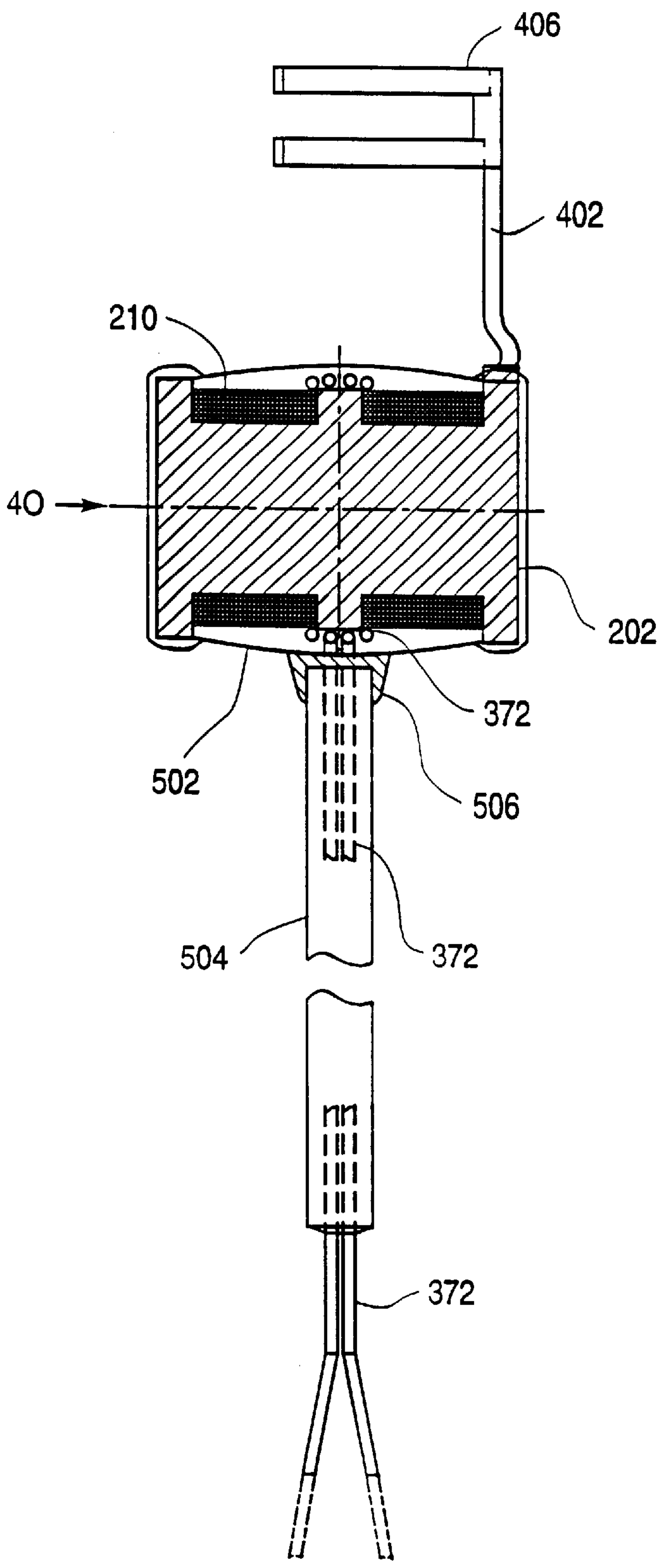
FIGS. 4N and 4O show views of a floating mass transducer that is ready to be implanted in a patient.
Figure 4O:
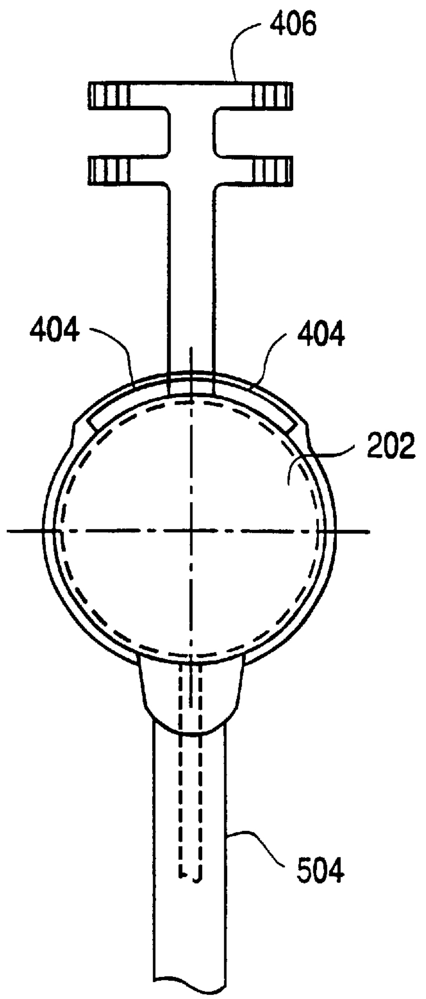

FIG. 4M shows views of a floating mass transducer that is ready to be implanted in a patient. The left side of the figure shows a cross-sectional view of the floating mass transducer. The housing includes a coating 502 which is made of a biocompatible material such as acrylic epoxy, biocompatible hard epoxy, and the like. Leads 372 are threaded through a sheath 504 which is secured to the housing with an adhesive 506. The right side of the figure shows the floating mass transducer along the line indicated by A.

Figure 5A:
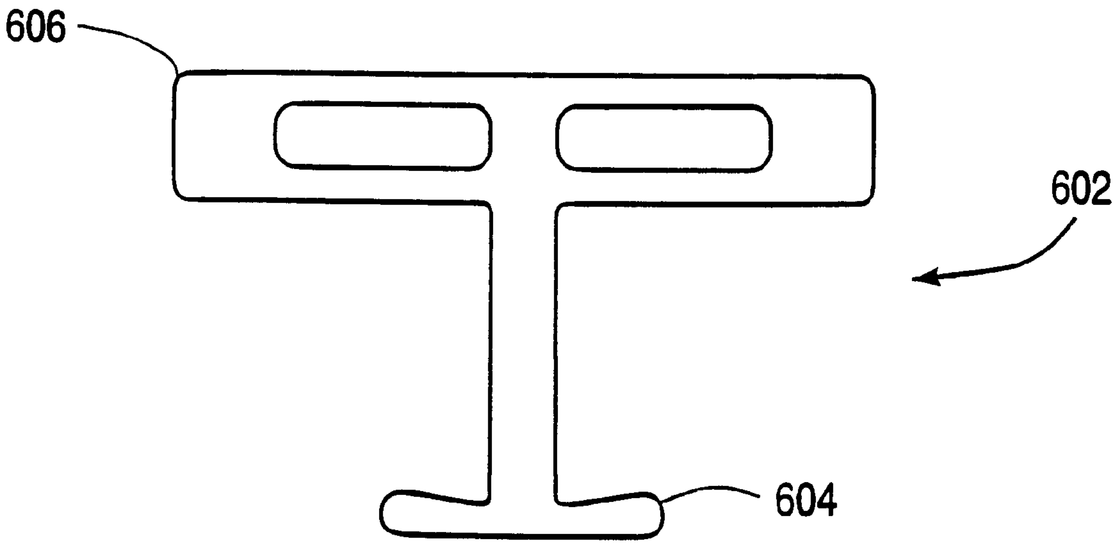
FIG. 5A shows another clip for connecting the floating mass transducer to an ossicle within the inner ear.

FIG. 5A shows another clip for connecting the floating mass transducer to an ossicle within the inner ear. A clip 602 has an end 604 that for attachment to the housing of the floating mass transducer and an end 606 that is curved in the form of a “C” so that it may be easily clamped on an ossicle like the incus. At end 606, the clip has rectangular prongs with openings therethrough.

Figure 5B:
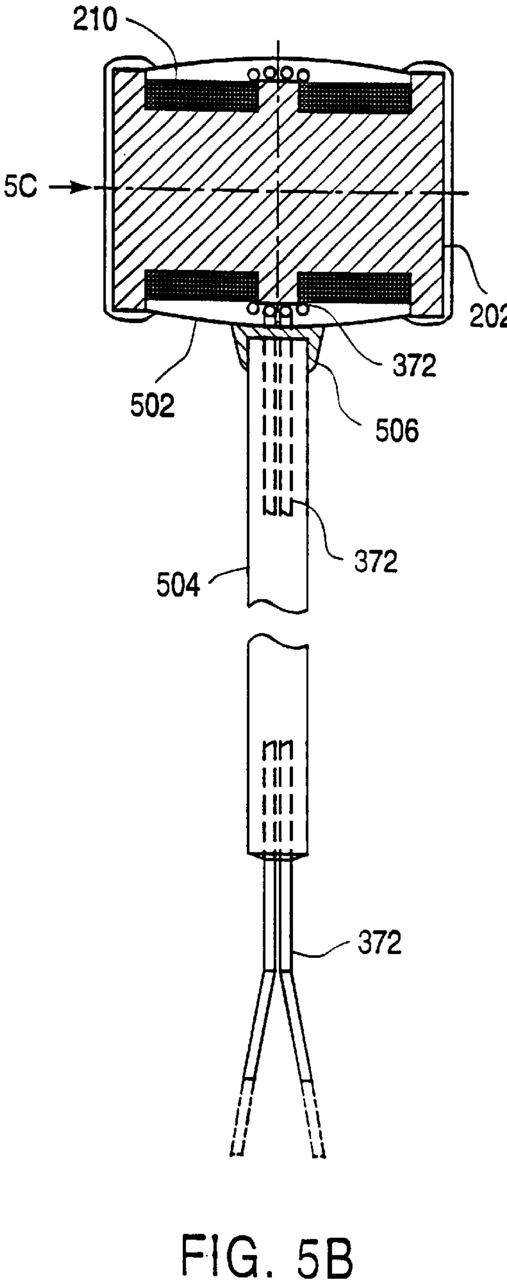
FIG. 5B shows views of another floating mass transducer that as ready to be implanted in a patient.
Figure 5C:
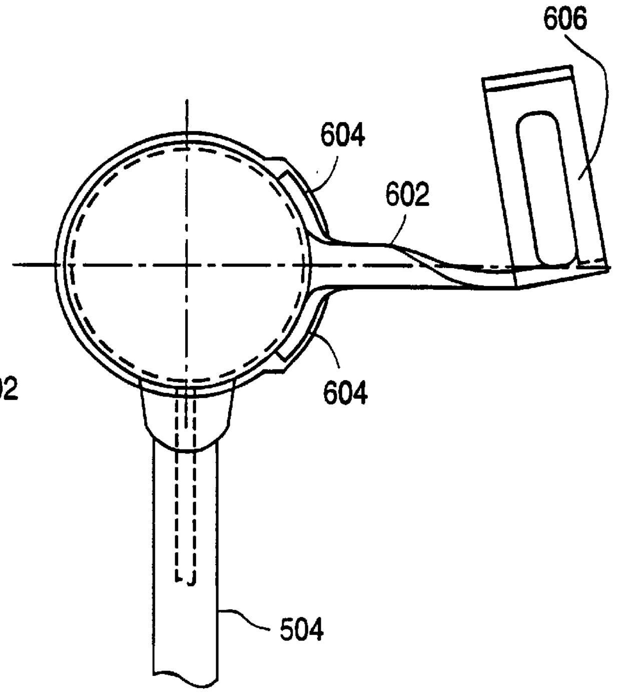
FIG. 5C is an end view of the apparatus of FIG. 5B.

FIG. 5B shows views of another floating mass transducer that is ready to be implanted in a patient. The left side of the figure shows a cross-sectional view of the floating mass transducer. As in FIG. 4M, the housing includes coating 502 and leads 372 are threaded through sheath 504 which is secured to the housing with adhesive 506. Clip 602 is not shown as the cross-section does not intercept the clip. However, the position of the clip is seen on the right side of the figure which shows the floating mass transducer along the line indicated by A.

Clip 602 extends away from the floating mass transducer perpendicular to leads 372. Additionally, the clip is twisted 90° to improve the ability to clip the floating mass Transducer to an ossicle.

While the above is a complete description of the preferred embodiments of the invention, various alternatives, modifications and equivalents may be used. It should be evident that the present invention is equally applicable by making appropriate modifications to the embodiments described above. Therefore, the above description should not be taken as limiting the scope of the invention which is defined by the metes and bounds of the appended claims along with their full scope of equivalents.

What is claimed is:

1. A method of manufacturing a hearing device, comprising:

providing a cylindrical housing;

placing a magnet within the housing;

biasing the magnet within the housing; and wrapping at least one coil around an exterior of the housing.

2. A method as in claim 1, wherein the magnet is placed within the housing so that an electrical signal through the at least one coil causes the magnet to vibrate relative to the housing.

3. A method as in claim 1, wherein the magnet is biased to permit inertial vibration of the housing.

4. A method as in claim 1, wherein the at least one coil is a pair of coils, each coil wound around the housing in opposite directions.

5. A method as in claim 1, further comprising sealing the housing.

6. A method as in claim 1, further comprising cutting a groove into the housing for each of the at least one coil, each of the at least one coil being wound around a groove.

7. A method as in claim 1, wherein the biasing comprises coupling a biasing mechanism to the magnet.

8. A method as in claims 7, wherein the biasing mechanism is coupled to the housing in order to restrict the magnet to linear movement within the housing.

9. A method as in claim 8, wherein the biasing comprises coupling a biasing mechanism which includes silicone.

10. A method for manufacturing a hearing device, comprising:

providing a housing having two ends;

coupling a pair of coils with an exterior of the housing; and positioning a cylindrical magnet within the housing so that an electrical signal through the pair of coils causes the magnet to vibrate relative to the housing, the vibration of the magnet causing inertial vibration of the housing.

11. A method as in claim 10, wherein the coupling comprises winding each coil of the pair of coils around the housing in opposite directions.

12. A method as in claim 10, wherein the housing includes two grooves on the exterior between the two ends, each coil being wound around a groove.

13. A method as in claim 10, wherein the housing is a sealed cylinder and at least one end is welded to seal the housing.

14. A method as in claim 10, wherein the positioning comprises coupling an end of the magnet to a pair of silicone biasing mechanisms, the biasing mechanisms biasing movement of the magnet within the housing.

15. A method as in claim 14, wherein each biasing mechanism is secured to the end of the magnet with an adhesive.

16. A method as in claim 14, wherein each end of the housing has an indentation on an interior of the housing so that each biasing mechanism is positioned partially within an indentation in order to restrict the magnet to linear movement within the housing.

* * * * *